US010898144B2

(12) United States Patent
Liu et al.

(10) Patent No.: US 10,898,144 B2
(45) Date of Patent: Jan. 26, 2021

(54) PHOTOPLETHYSMOGRAPHY (PPG) INDICATION DISCONTINUITY DETECTION AND CORRECTION

(71) Applicant: Microsoft Technology Licensing, LLC, Redmond, WA (US)

(72) Inventors: Zongyi Liu, Redmond, WA (US); Haithem Albadawi, Redmond, WA (US); Han Yee Mimi Fung, Bellevue, WA (US); Christopher Nuesmeyer, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 778 days.

(21) Appl. No.: 15/359,171

(22) Filed: Nov. 22, 2016

(65) Prior Publication Data
US 2018/0140253 A1    May 24, 2018

(51) Int. Cl.
*A61B 5/00* (2006.01)
*A61B 5/024* (2006.01)

(52) U.S. Cl.
CPC .......... *A61B 5/742* (2013.01); *A61B 5/02427* (2013.01); *A61B 5/725* (2013.01); *A61B 5/7221* (2013.01); *A61B 5/02433* (2013.01); *A61B 5/6824* (2013.01); *A61B 2503/10* (2013.01)

(58) Field of Classification Search
CPC .............................. A61B 5/742; A61B 5/7221
See application file for complete search history.

(56) References Cited

U.S. PATENT DOCUMENTS

| 8,948,832 | B2 | 2/2015 | Hong et al. |
| 9,149,196 | B2 | 10/2015 | Rodriguez-Llorente et al. |
| 9,259,186 | B2* | 2/2016 | Rodriguez-Llorente ........ A61B 5/7203 |
| 2003/0073886 | A1* | 4/2003 | Yanagidaira ............ A61B 5/18 600/300 |
| 2008/0249382 | A1* | 10/2008 | Oh ........................ A61B 5/6826 600/324 |
| 2010/0286495 | A1 | 11/2010 | Mcgonigle et al. |
| 2010/0298676 | A1 | 11/2010 | Addison et al. |
| 2014/0073943 | A1 | 3/2014 | Rodriguez-llorente et al. |
| 2014/0175261 | A1 | 6/2014 | Addison et al. |
| 2014/0213863 | A1 | 7/2014 | Loseu et al. |

(Continued)

OTHER PUBLICATIONS

Kim, et al., "Low-Power Photoplethysmogram Acquisition Integrated Circuit with Robust Light Interference Compensation", In Journal of Sensors, vol. 16, Issue 1, Dec. 31, 2015, 1-11.

(Continued)

*Primary Examiner* — Hien N Nguyen
(74) *Attorney, Agent, or Firm* — Arent Fox LLP (57) ABSTRACT

Methods and devices for heart rate monitoring may include determining whether an adjustment triggering condition has been met. Moreover, the methods and devices may include, in accordance with a determination that the adjustment triggering condition has been met, adjusting the second sensor indication to obtain an adjusted second sensor indication based at least on the difference between the first sensor indication and the second sensor indication. The methods and devices may further include, in accordance with a determination that the adjustment triggering condition has not been met, transmitting the second sensor indication to the signaling filter.

20 Claims, 8 Drawing Sheets

(56) References Cited

U.S. PATENT DOCUMENTS

2014/0275888 A1    9/2014  Wegerich et al.
2016/0213267 A1*   7/2016  Laakkonen ........ A61B 5/02433
2017/0170852 A1*   6/2017  Kwon ............... H04L 25/03261

OTHER PUBLICATIONS

Khan, et al., "A Robust Heart Rate Monitoring Scheme Using Photoplethysmographic Signals Corrupted by Intense Motion Artifacts", In Journal of IEEE Transactions on Biomedical Engineering, vol. 63, Issue 3, Mar. 2016, 550-562.

Lee, Junyeon, "Motion artifacts reduction from PPG using cyclic moving average filter", In Journal of Technology and Health Care, vol. 22, No. 3, Jan. 1, 2014, 1 pages.

* cited by examiner

PHOTOPLETHYSMOGRAPHY (PPG) INDICATION DISCONTINUITY DETECTION AND CORRECTION

BACKGROUND

The present disclosure relates to electronic devices, and more particularly, to correcting photoplethysmography (PPG) indication/signal discontinuity detection and correction at a wearable electronic device.

Use of computing devices is becoming more ubiquitous by the day. Computing devices range from standard desktop computers to wearable computing technology and beyond. The field of wearable devices has grown in recent years with the introduction of fitness bands and smart watches, some of which can interface with a nearby mobile device via short range communication technology (e.g., Bluetooth) to provide information thereto and/or to obtain and display information therefrom for consumption by a user wearing the fitness band or smart watch. These devices may include global positioning systems (GPS), altimeters, and stopwatches, for example, and may track a user's speed, position and time while running, bicycling, skiing, etc.

One problem with such devices is that they typically do not present the user with accurate information other than time and position information. Further, the use of other sensors, such as PPG heart rate or pulse sensors that use a light-based technology to sense the rate of blood flow as controlled by the heart's pumping action, may not provide accurate PPG readings during various activities or in certain environments.

Thus, there is a need in the art for improvements in PPG detection in a wearable electronic device.

SUMMARY

The following presents a simplified summary of one or more implementations in order to provide a basic understanding of such implementations. This summary is not an extensive overview of all contemplated implementations, and is intended to neither identify key or critical elements of all implementations nor delineate the scope of any or all implementations. Its purpose is to present some concepts of one or more implementations in a simplified form as a prelude to the more detailed description that is presented later.

In one example, a method of heart rate monitoring at an electronic device is provided. In particular, the method may include, while continuing operation of a signaling filter in communication with a processor receiving a first sensor indication associated with a first heart rate detection at a first time. The method may further include receiving a second sensor indication associated with a second heart rate detection at a second time after the first time. Additionally, the method may include determining whether an adjustment triggering condition has been met. Moreover, the method may include, in accordance with a determination that the adjustment triggering condition has been met, adjusting the second sensor indication to obtain an adjusted second sensor indication based at least on the difference between the first sensor indication and the second sensor indication. In addition, the method may include, in accordance with a determination that the adjustment triggering condition has not been met, transmitting the second sensor indication to the signaling filter.

In another example, an electronic device for heart rate monitoring comprising a memory configured to store data and instructions, at least one sensor configured to obtain one or more sensor indications, a signaling filter to filter the one or more sensor indications, and a processor in communication with the memory and the at least one sensor. The processor may, while continuing operation of the signaling filter, be configured to receive, from the at least one sensor, a first sensor indication associated with a first heart rate detection at a first time. The processor may further be configured to receive, from the at least one sensor, a second sensor indication associated with a second heart rate detection at a second time after the first time. Additionally, the processor may be configured to determine whether an adjustment triggering condition has been met. Moreover, the processor may be configured to, in accordance with a determination that the adjustment triggering condition has been met, adjust, by the processor, the second sensor indication to obtain an adjusted second sensor indication based at least on the difference between the first sensor indication and the second sensor indication. In addition, the processor may be configured to, in accordance with a determination that the adjustment triggering condition has not been met, transmit the second sensor indication to the signaling filter.

In a further example, a computer-readable medium storing instructions executable by an electronic device for heart rate monitoring. The computer-readable medium may include at least one instruction for causing the computer device to receive a first sensor indication associated with a first heart rate detection at a first time. The computer-readable medium may further include at least one instruction for causing the computer device to receive a second sensor indication associated with a second heart rate detection at a second time after the first time. Moreover, the computer-readable medium may include at least one instruction for causing the computer device to determine whether an adjustment triggering condition has been met. Additionally, the computer-readable medium may include at least one instruction for causing the computer device to, in accordance with a determination that the adjustment triggering condition has been met, adjust the second sensor indication to obtain an adjusted second sensor indication based at least on the difference between the first sensor indication and the second sensor indication while continuing operation of a signaling filter. In addition, the computer-readable medium may include at least one instruction for causing the computer device to, in accordance with a determination that the adjustment triggering condition has not been met, transmit the second sensor indication to the signaling filter.

Additional advantages and novel features relating to implementations of the present disclosure will be set forth in part in the description that follows, and in part will become more apparent to those skilled in the art upon examination of the following or upon learning by practice thereof.

DESCRIPTION OF THE FIGURES

The specific features, implementations, and advantages of the disclosure will become better understood with regard to the following description, appended claims, and accompanying drawings where:

DETAILED DESCRIPTION

The detailed description set forth below in connection to the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts. In some implementations, examples may be depicted with references to one or more components and one or more methods that may perform the actions or operations described herein, where components and/or actions/operations in dashed line may be optional.

The present disclosure relates to detecting and correcting photoplethysmography (PPG) signal/indication discontinuity at a wearable electronic device. For example, wearable electronic devices may be used (e.g., worn on a wrist) by a user during various activities. Such activities may include, but are not limited to, walking, running, or any other activity that may result in a change in a heart rate of a user. Further, some wearable electronic devices may include at least a PPG sensor in the form of an optical sensing device to measure or otherwise detect a PPG signal or indication corresponding to a heart rate of a user. For example, a PPG sensor may include a light source directed into the tissue of the user, and a detector to detect backscattered or transmitted light that corresponds to a variation in the blood volume. Such detected light may be referred to as a PPG signal or indication, or may be converted into a PPG signal or indication. As such, in some implementations, a PPG signal/indication may provide a measurement of a reflection of light from, or transmission of light through, a user's capillaries over a period of time.

During light detection or sensing by the PPG sensor, however, leaking ambient light and/or changes in the intensity of the light source (e.g., a light emitting diode (LED) in the PPG sensor) may result in discontinuity of the PPG signal measurements at particular points in time. The discontinuity may be indicative of a distorted PPG signal in a sequence of PPG signal measurements caused by leaking ambient light and/or changes in LED light intensity. In operation, as with the other PPG signals in the sequence of measurements, the distorted PPG signal or indication may be fed to a signaling filter for sampling and noise filtering. If the distorted PPG signal is fed into the signaling filter, however, the filtered signal may correspondingly become distorted for a period of time, resulting in a potential inaccurate heart rate estimation. Further, resetting the signaling filter when encountering discontinuity (e.g., a distorted PPG signal) may result in a delay until enough PPG data is subsequently obtained to form an accurate filtered signal.

In an example, the filtering of the PPG signals/indications on a wearable electronic device, such as a wrist band, may be performed in real-time. In some instances, a finite impulse response (FIR) filter may be utilized due to its stability and lack of feedback utilization. However, an FIR filter may also have a long delay, which means that the latest filter output is a few seconds behind the input. On the other hand, a PPG signal/indication of a wearable electronic device may have a discontinuity problem due to an LED light intensity that is adjusted from time-to-time for a better signal-to-noise (SNR) ratio. In such instances, the input signal may have a large delta (e.g., change in value) in at least a few samples (PPG signals), and as such, this sharp change may impact the FIR filter for some time resulting in a distorted output. One solution may be to reset the FIR filter when the discontinuity occurs, but this solution may result in a loss of a portion of PPG measurement data (corresponding to the delay time). For example, if the FIR filter has a delay of 'X' seconds, and at time 't' the discontinuity occurs resulting in a reset of the FIR filter, then the filtered data between [t–X, t] may be lost.

The present implementations provide a PPG signal/indication discontinuity detection and correction mechanism for robust FIR filtering. In particular, discontinuity in a PPG signal/indication stream may be detected and corrected without resetting a signal filter, such as an FIR filter. For example, the present implementations may correct a distorted or discontinuous PPG signal/indication by shifting the PPG signal/indication in a vertical direction (e.g., up or down) without resetting the signaling filter. By shifting or adjusting the distorted or discontinuous PPG signal/indication, the signaling filter may not lose PPG measurement data, and thus, its output may be minimally impacted by the distorted or discontinuous PPG signal/indication. Accordingly, the present implementations may be applied selectively and immediately to a distorted or discontinuous PPG signal/indication for instantaneous correction to allow continuous operation of the signaling filter.

Figure 1A:
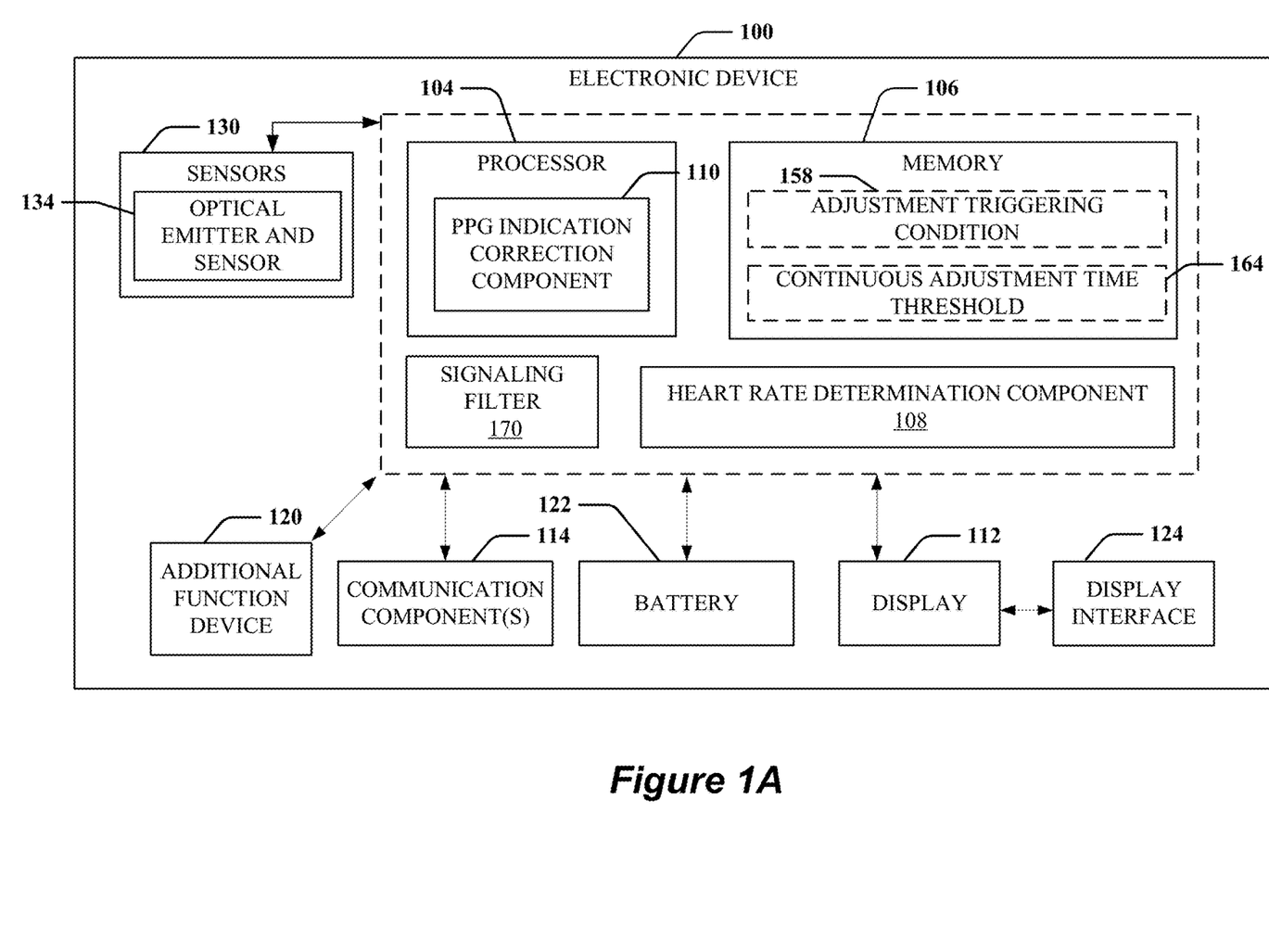
FIG. 1A is a schematic block diagram of an example electronic device including an photoplethysmography (PPG) indication correction component in accordance with some implementations.
Figure 1B:
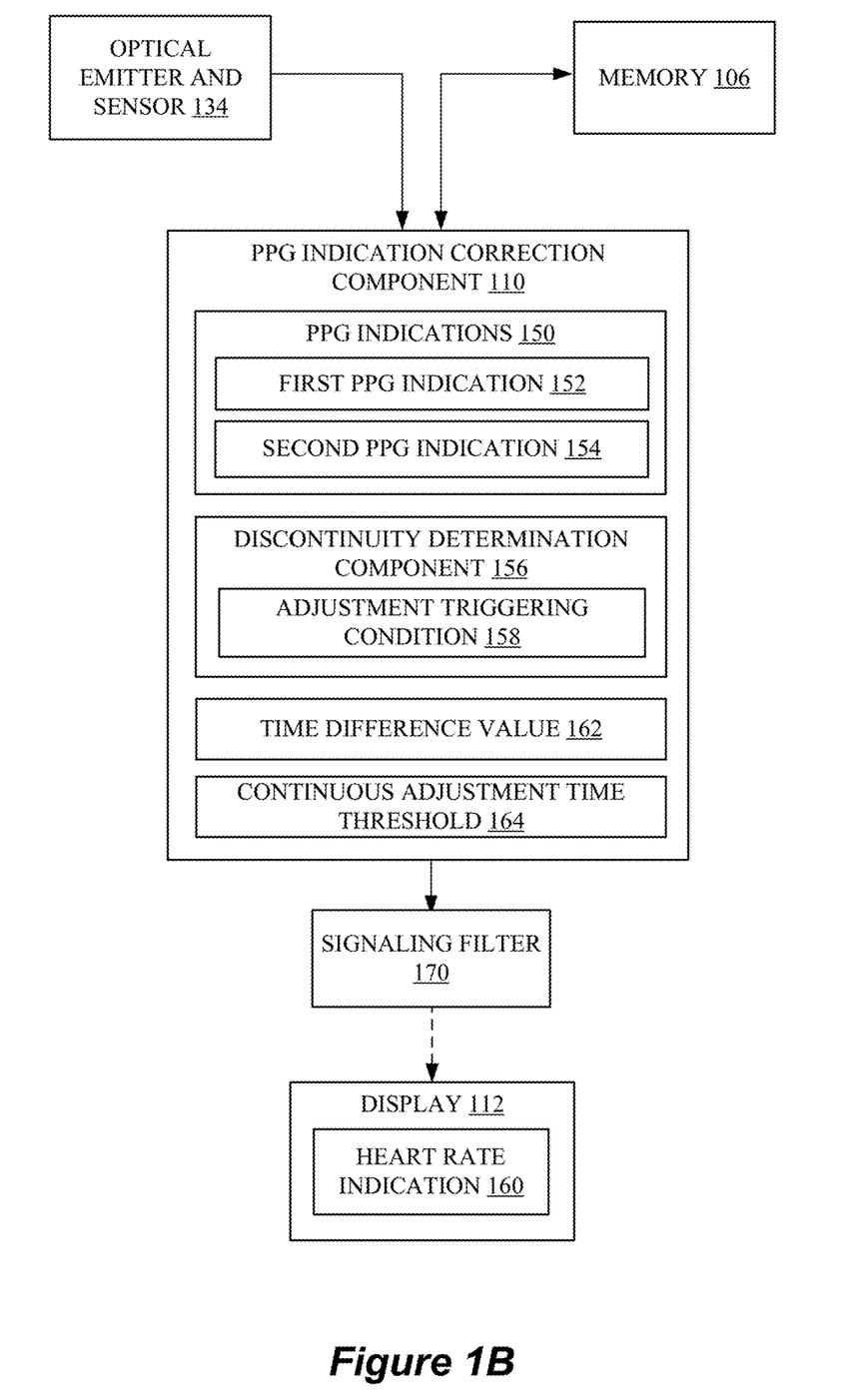
FIG. 1B is a schematic block diagram of the PPG indication detection and correction component and various subcomponents in accordance with some implementations.

Referring now to FIGS. 1A and 1B, an example electronic device 100 may include one or more components and/or subcomponents such as a PPG indication correction component 110 for detecting and correcting one or more PPG indications 150 associated with a user of the electronic device 100, where at least some of the one or more PPG indications 150 may be discontinuous. In some implementations, the electronic device 100 may be or otherwise take the form of a smart watch, fitness band, and/or other wearable device. In some implementations, the electronic device 100 may include or may otherwise be coupled with a processor 104 and/or a memory 106, where the processor 104 and/or the memory 106 may be configured to execute or store instructions or other parameters, such as an adjustment triggering condition 158 and/or a continuous adjustment time threshold 164, related to executing a PPG indication correction component 110 for detecting and correcting the one or more PPG indications 150 of a user of the electronic device 100. For example, the PPG indication correction component 110 can correspond to an operating system of the electronic device 100 (e.g., a mobile operating system) or an application executing on the operating system of the electronic device 100.

In some implementations, the electronic device 100 may also include a display 112 having a presentation area, such as a screen, for presenting one or more graphical interfaces (e.g., graphical user interfaces (GUI)), such as to provide information for consumption by a user wearing the electronic device 100. For example, the display 112 may be or may include a liquid crystal display (LCD), light emitting diode (LED), organic LED (OLED), high-contrast electronic ink (E-Ink), a fabric including light pipes, or a micro-LED array, and may display graphical interfaces as instructed by processor 104 (e.g., based on execution of the PPG indication correction component 110).

The electronic device 100 may also include a display interface 124 that couples to display 112 to provide instructions, parameters, or signals, for example, for displaying the graphical interfaces. In some implementations, the display 112 and/or the display interface 124 may form a touch-sensitive display that may detect touch inputs on the display 112 (e.g., for interacting with a user interface) and also output data in the form of graphical representations (e.g., on the user interface).

In some implementations, the electronic device 100 may also include one or more communication component(s) 114 for communicating with another device via a wired or wireless interface (Bluetooth, radio frequency identification (RFID), near field communication (NFC)). The electronic device 100 may also include a battery 122 for providing power to various components and/or subcomponents of the electronic device 100.

In some implementations, the electronic device 100 may also include one or more sensors 130, which may include an optical emitter and sensor 134 for transmitting and detecting light to and from a capillary of a user of the electronic device 100. The optical emitter and sensor 134 may detect backscatter from the transmitted light, which may be used to determine one or more PPG indications/signals 150 corresponding to a heart rate of the user.

In some implementations, the one or more sensors 130 may also include an accelerometer for detecting at least acceleration of the electronic device 100, a gyroscopic sensor for detecting angular velocity of the electronic device 100, an angle or orientation sensor for detecting a position of the electronic device 100 relative to a reference plan, a compass for determining a direction of magnetic north and bearing from it, an ultraviolet (UV) sensor for detecting light in the ultraviolet spectrum, and/or a barometer for measuring atmospheric pressure.

In addition, the electronic device 100 may include one or more additional function devices 120 for providing additional functionality to the electronic device 100. For example, the one or more additional function devices 120 may include but are not limited to a global positioning system (GPS) radio, a fitness tracking device (e.g., a step tracking device, a pulse monitor or tracking device, a power meter, or any other type of fitness- or biometric-characteristic tracking device), a battery, a microphone, a galvanic skin sensor, a memory, a processor, or a communication interface, such as an RFID radio, Bluetooth radio, or a Wi-Fi radio.

In some implementations, the electronic device 100 may include an operating system executed by the processor 104 and/or the memory 106 of the electronic device 100. The memory 106 may be configured for storing data and/or computer-executable instructions defining and/or associated with the operating system (and/or firmware), and the processor 104 may execute the operating system and/or one or more associated components such as the PPG indication correction component 110. An example of the memory 106 can include, but is not limited to, a type of memory usable by a computer, such as random access memory (RAM), read only memory (ROM), tapes, magnetic discs, optical discs, volatile memory, non-volatile memory, and any combination thereof. An example of the processor 104 may include, but is not limited to, any processor specially programmed as described herein, including a controller, microcontroller, application specific integrated circuit (ASIC), field programmable gate array (FPGA), system on chip (SoC), or other programmable logic or state machine.

Referring more specifically to FIG. 1B, the PPG indication correction component 110 may at least detect and correct a PPG discontinuity in the one or more PPG indications 150. In particular, as part of monitoring or continuously determining a user's heart/pulse rate, the PPG indication correction component 110 may be configured to receive one or more PPG indications 150 from, for example, the optical emitter and sensor 134. As the PPG indication correction component 110 receives each of the one or more PPG indications 150, which may take the form of optical signals or measurements, a determination may be made by the discontinuity determination component 156 as to whether an adjustment triggering condition 158 has been met. In some implementations, as part of determining whether the adjustment triggering condition 158 has been met, the discontinuity determination component 156 may be configured to determine whether the second sensor indication is associated with a discontinuity flag. For example, the discontinuity flag may be indicative of a change or an adjustment of an LED light source of the optical emitter and sensor 134 during measurement acquisition. That is, PPG indication correction component 110 may be configured to receive one or more PPG indications 150, some of which may include or otherwise are associated with the discontinuity flag representing a change or adjustment of the LED light source of the optical emitter and sensor 134 during acquisition of at least some of the one or more PPG indications 150.

The discontinuity determination component 156 may determine whether a PPG indication that is received from the optical emitter and sensor 134 is discontinuous or distorted, which may be indicated by a change in value from a prior PPG indication (e.g., between the first PPG indication 152 and the second PPG indication 154). For instance, a discontinuous or distorted PPG indication may be caused by ambient light leakage onto the optical emitter and sensor 134. Upon determining that a PPG indication, such as the second PPG indication 154, is discontinuous or distorted, the PPG indication correction component 110 may be configured to adjust, in a gradual and/or continuous manner, the distorted PPG indication 150 (e.g., the second PPG indication 154) for a period of time. Specifically, each of the one or more PPG indications 150 may include a pulsating alternating current (AC) component and a non-pulsating direct current (DC) component. The PPG indication correction component 110 may be configured to adjust the distorted PPG indication by shifting the DC component of the distorted PPG indication up or down depending on the direction of distortion, as is explained below in more detail.

The principle behind the optical emitter and sensor 134 (alternatively referred to as a PPG sensor) is optical detection of blood volume changes in a microvascular bed of the tissue. The sensor system may include a light source and a detector, with red and infrared (IR) light-emitting diodes (LEDs) used as the light source. The optical emitter and sensor 134 may monitor changes in the light intensity via reflection from or transmission through a user's tissue. The changes in light intensity may be associated with small variations in blood perfusion of the tissue and provide information on the cardiovascular system, in particular the pulse and/or heart rate associated with or corresponding to at least one of the one or more PPG signals/indications 150.

The one or more PPG indications 150 may each provide or otherwise include a heart rhythm pulsating alternating current (AC) component, and a non-pulsating DC component. The DC component of the signal may represent a light absorption in the tissue bed, bone, venous blood, capillary blood, and/or non-pulsatile arterial blood. The AC component may capture the pulsating arterial blood. In other words, the DC component of the one or more PPG indications 150 may be attributable to the light absorption of the skin tissue, while the AC component may be directly attributable to variation in blood volume in the skin caused by the pressure pulse of the cardiac cycle. The fundamental frequency of the AC component depends on the heart rate and may be superimposed onto the DC component, which changes with or may be correlated to changes in respiration.

If the PPG indication (e.g., the second PPG indication 154) is distorted in a downward direction (indicative of low light detection), the PPG indication correction component 110 may be configured to shift, gradually or incrementally, the DC component of the PPG indication in an upward direction until a time difference value 162 between a current time and the time the discontinuity or distortion occurred satisfies (e.g., is greater than or equal to) a continuous adjustment time threshold 164, which may be a time value indicative of a gap between an occurrence of the PPG discontinuity. Alternatively, or in conjunction, if the PPG indication (e.g., the second PPG indication 154) is distorted in a downward direction, the PPG indication correction component 110 may be configured to shift, gradually or incrementally, the DC component of the PPG indication in an upward direction until an amplitude difference value representing a delta of an amplitude (DC component) between the PPG indication and a previous (undistorted) PPG indication converges with the undistorted PPG indication representing the heart rate/pulse detection occurring after the distorted PPG indication. In some implementations, convergence may occur when the amplitude difference value satisfies a convergence threshold corresponding to a minimum difference value between PPG indication amplitudes.

Similarly, if the PPG indication (e.g., the second PPG indication 154) is distorted in an upward direction (indicative of large light detection), the PPG indication correction component 110 may be configured to shift, gradually or incrementally, the DC component of the PPG indication in a downward direction until a time difference value 162 between a current time and the time the discontinuity or distortion occurred satisfies the continuous adjustment time threshold 164. Alternatively, or in conjunction, if the PPG indication (e.g., the second PPG indication 154) is distorted in a upward direction, the PPG indication correction component 110 may be configured to shift, gradually or incrementally, the DC component of the PPG indication in a downward direction until an amplitude difference value representing a delta of an amplitude (DC component) between the PPG indication and a previous (undistorted) PPG indication converges with the undistorted PPG indication representing the heart rate/pulse detection occurring after the distorted PPG indication.

Figure 3A:
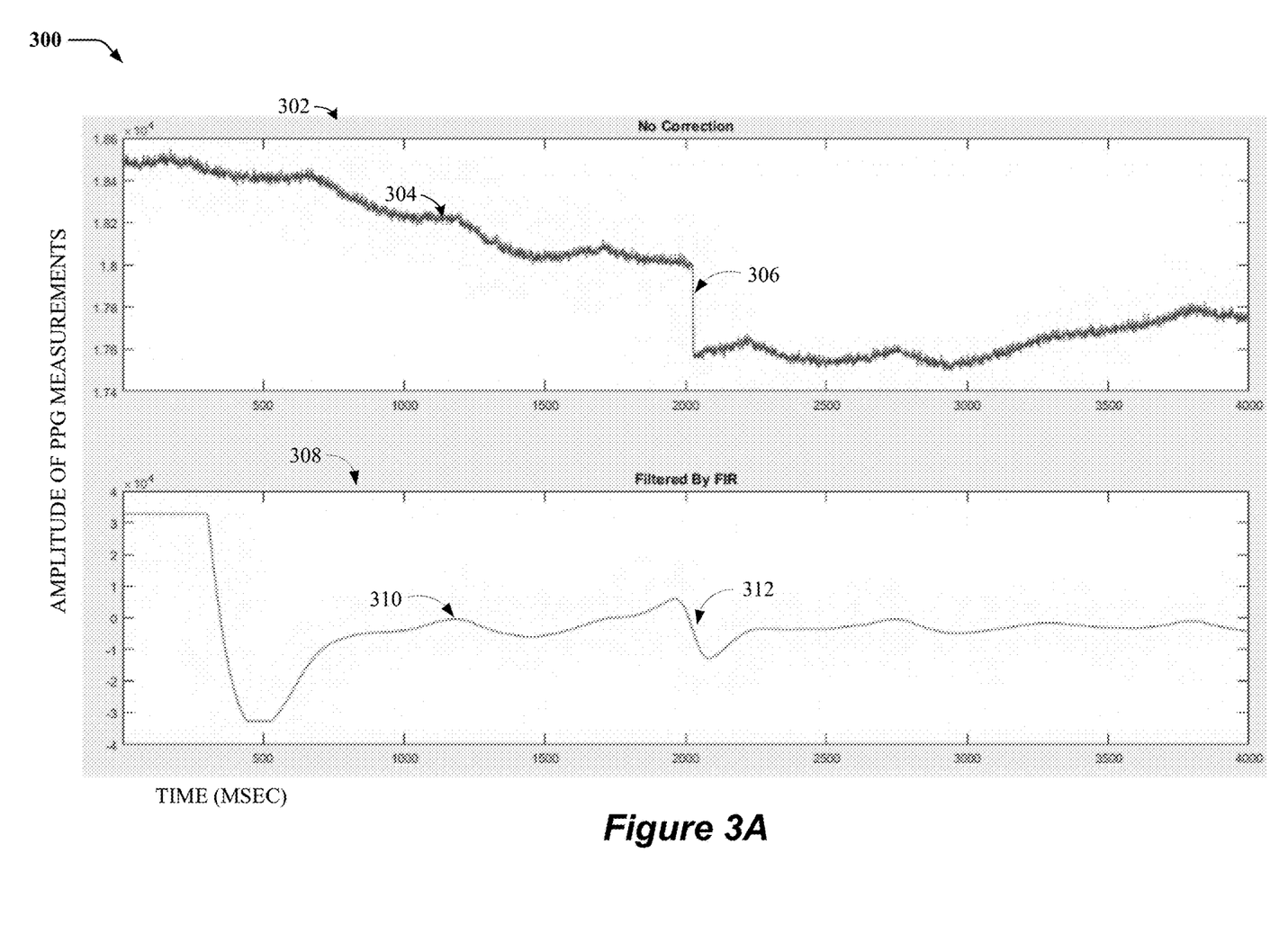
FIG. 3A is a graphical representation of example PPG measurements in accordance with some implementations.
Figure 3B:
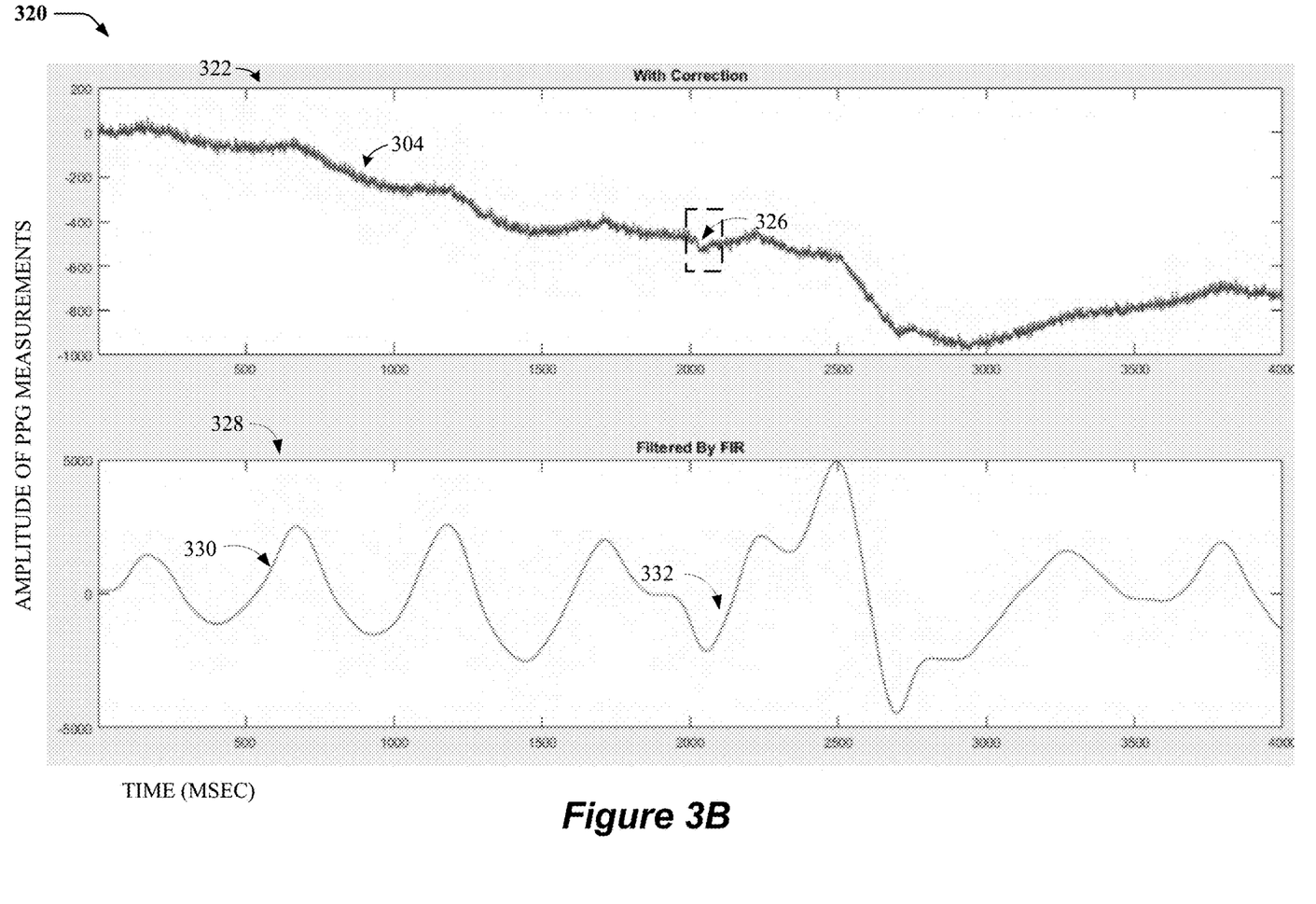
FIG. 3B is a graphical representation of another example PPG measurements in accordance with some implementations

As such, in operation, to effectively smooth or correct the distorted PPG indication (e.g., as shown in FIG. 3A), the PPG indication correction component 110 may shift by an order of magnitude along the y-axis (e.g., vertically by 1 unit of amplitude every 4 samples/indications), decrement the time difference value 162 and/or an amplitude difference value, and continue shifting again until the time difference value 162 no longer satisfies the continuous adjustment time threshold 164 (e.g., as shown in FIG. 3B), and/or the amplitude difference value converges with the undistorted PPG indication. In some implementations, the adjustment or shifting of the DC component may occur after a time period (e.g., 1 sec) following the discontinuity event (e.g., following the second time).

The corrected PPG indications may then be fed or transmitted to the signaling filter 170, such as an FIR filter, which, without resetting, may down-sample, noise filter, and then up-sample the received PPG indications. As such, the PPG indication correction component 110 may be configured to detect a discontinuity between adjacent PPG signals/indications and correct a distorted PPG indication while the signaling filter continues to operate (e.g., without resetting the signaling filter). The filtered PPG indication may be provided, at a point in the processing stream, to the heart rate determination component 108, which may be configured to determine a heart rate indication 160 that corresponds to the detected PPG indication. Any remaining artifacts resulting from the correction approach may be eliminated/smoothed by filtering at the signaling filter 170 and/or by the PPG indication correction component 110. Further, the heart rate determination component 108 may provide the heart rate indication 160 to the display 112 for displaying the heart (or pulse) rate indication 160 to a user without much delay between PPG indication detection and filtering by the signaling filter 170.

Figure 2:
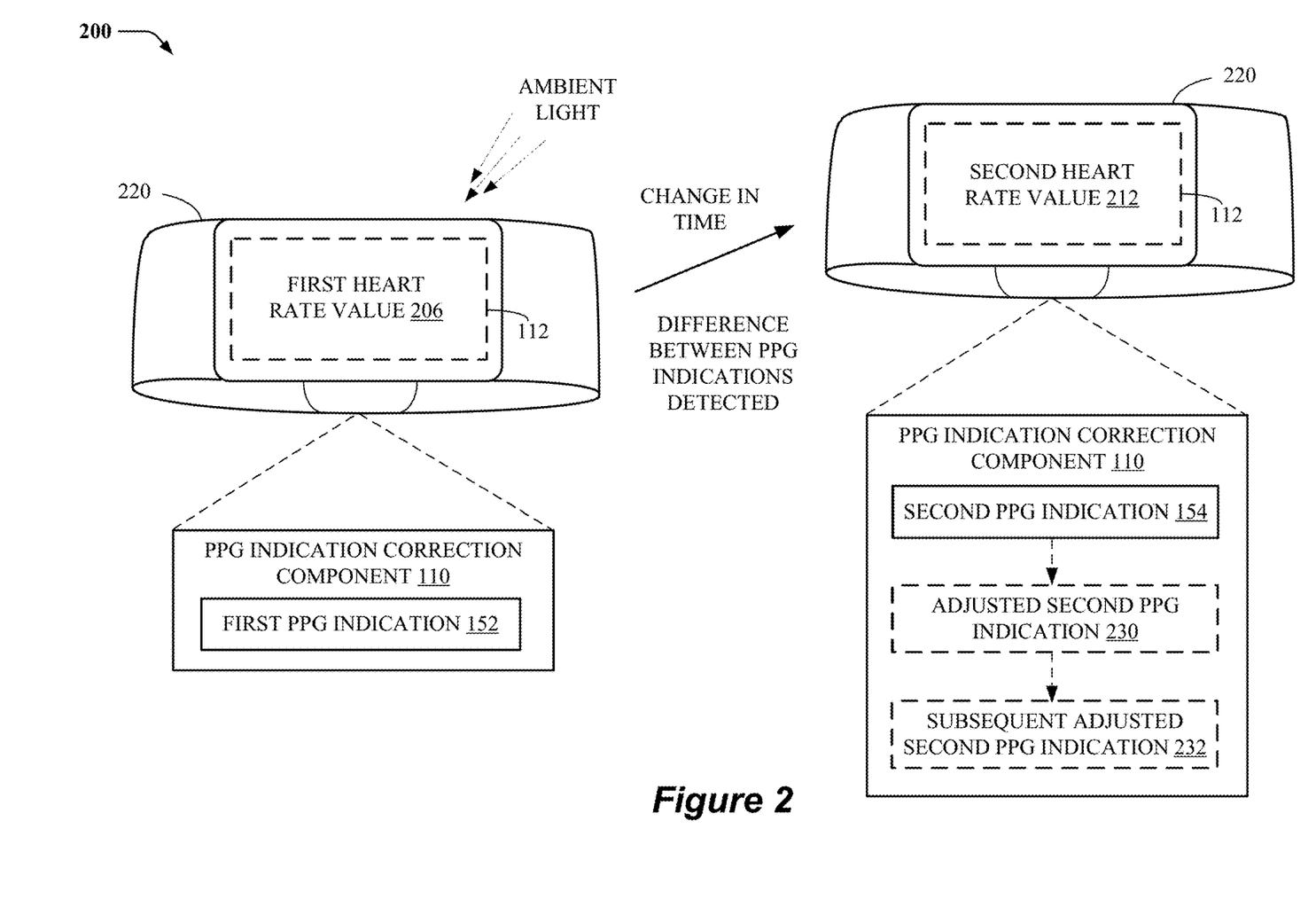
FIG. 2 is a conceptual diagram of PPG indication/signal detection and correction at an example wearable electronic device in accordance with some implementations.

Referring now to FIG. 2, a conceptual diagram 200 is shown of an example wearable electronic device 220 displaying heart/pulse rate values associated with respective PPG signals/indications based on an optical measurement of a user's capillaries by the optical emitter and sensor 134 (FIGS. 1A and 1B) integrated with the wearable electronic device 220, in accordance with some implementations. The conceptual diagram 200 illustrates the capability of the wearable electronic device 220 to determine and display two distinct heart rate values even during instances where discontinuity between adjacent PPG signals may occur by, for example, ambient light on the optical emitter and sensor 134 (FIGS. 1A and 1B). Specifically, the wearable electronic device 220 may include the PPG indication correction component 110, which may correct a distorted PPG indication associated with a heart/pulse rate detection in real-time without resetting a signaling filter, such as an FIR filter. In some implementations, the wearable electronic device 220 may be the same as or similar to electronic device 100 (FIG. 1A).

While continuing operation of the signaling filter 170 (FIG. 1B) such as an FIR filter, the wearable electronic device 220 may detect (e.g., via optical emitter and sensor 134, FIGS. 1A and 1B) the first PPG indication 152 associated with a first heart/pulse rate detection at a first time, which may not exhibit distorted characteristics as determined by the discontinuity determination component 156 (FIG. 1B). As such, the first PPG indication 152 may be fed to the signaling filter 170 (FIG. 1B) for subsequent presentation in the form of a first heart rate value 206 (e.g., as determined by the heart rate determination component 108 (FIG. 1A)) on the display 112.

At a second time after the first time, the PPG indication correction component 110 may receive, from the optical emitter and sensor 134 (FIGS. 1A and 1B), the second PPG indication 154 associated with a second heart/pulse rate detection. As a result of the ambient light detected during measurement of the second PPG indication 154, the second PPG indication 154 may be distorted such that feeding the second PPG indication 154 to the signaling filter 170 (FIG. 1B) without correction would result in a distorted output signal, and potentially an inaccurate second heart rate value 212.

In this case, the PPG indication correction component 110 may detect a discontinuity between the first PPG indication 152 and the second PPG indication 154. As such, the PPG indication correction component 110 may correct the second PPG indication 154 by shifting its DC component by an order of magnitude (e.g., adjust an amplitude of the second PPG indication 154). For example, the PPG indication correction component 110 may initially shift the DC component of the second PPG indication 154 to obtain an adjusted second PPG indication 230, which may then be provided to the signaling filter 170 (FIG. 1B).

Additionally, if the PPG indication correction component 110 continues to determine to shift the DC component of the second PPG indication 154 based on the time difference value 162 (FIG. 1B) satisfying the continuous adjustment time threshold 164 (FIG. 1B), a subsequent adjusted second PPG indication 232 may be obtained by shifting the DC component of the adjusted second PPG indication 230 by another order of magnitude. The subsequent adjusted second PPG indication 232 may be provided to signaling filter 170 (FIG. 1B) for sampling and noise filtering. Display 112 may then present the second heart rate value 212 (e.g., as determined by the heart rate determination component 108, FIG. 1A) associated with the subsequent adjusted second PPG indication 232.

FIGS. 3A and 3B are example graphical representations 300 and 320 of PPG measurements without correction (e.g., in graphical representation 300) and with correction (e.g., in graphical representation 320) by the PPG indication correction component 110 (FIGS. 1A and 1B). Each graph includes a representation in an amplitude of PPG measurements over time (e.g., in milliseconds) in accordance with some implementations.

The graphical representation 300 of FIG. 3A includes a PPG indication measurement without correction graph 302, and a corresponding filtered PPG indication measurement without correction graph 308. As shown in the PPG indication measurement without correction graph 302, the PPG indication measurements 304 encounter a discontinuity event 306, where a PPG indication at approximately time 2000 milliseconds (msec) exhibits a large sudden drop in amplitude. The corresponding filtered PPG indication measurements 310 in the corresponding filtered PPG indication measurement without correction graph 308 may also exhibit a corresponding distortion 312 at approximately the same time (e.g., beginning at 2000 msec).

On the other hand, in FIG. 3B, the graphical representation 320 illustrates a correction of the discontinuity event 306 evident in PPG indication measurement without correction graph 302, and notably in the PPG indication measurements 304, based on implementation of the present disclosure. For instance, the corrected PPG indication measurement graph 322 includes, at approximately 2000 msec, one or more corrected PPG indications 326 that have been shifted up by an order of magnitude to a corrected or shifted PPG indication position (e.g., by the PPG indication correction component 110, FIGS. 1A and 1B). Accordingly, the corresponding corrected filtered PPG indication measurement graph 328 may include filtered PPG indication measurements 330 that are not distorted at the time (e.g., approx. 2000 msec) of or region of discontinuity 332 as a result of the PPG indication correction.

Figure 4A:
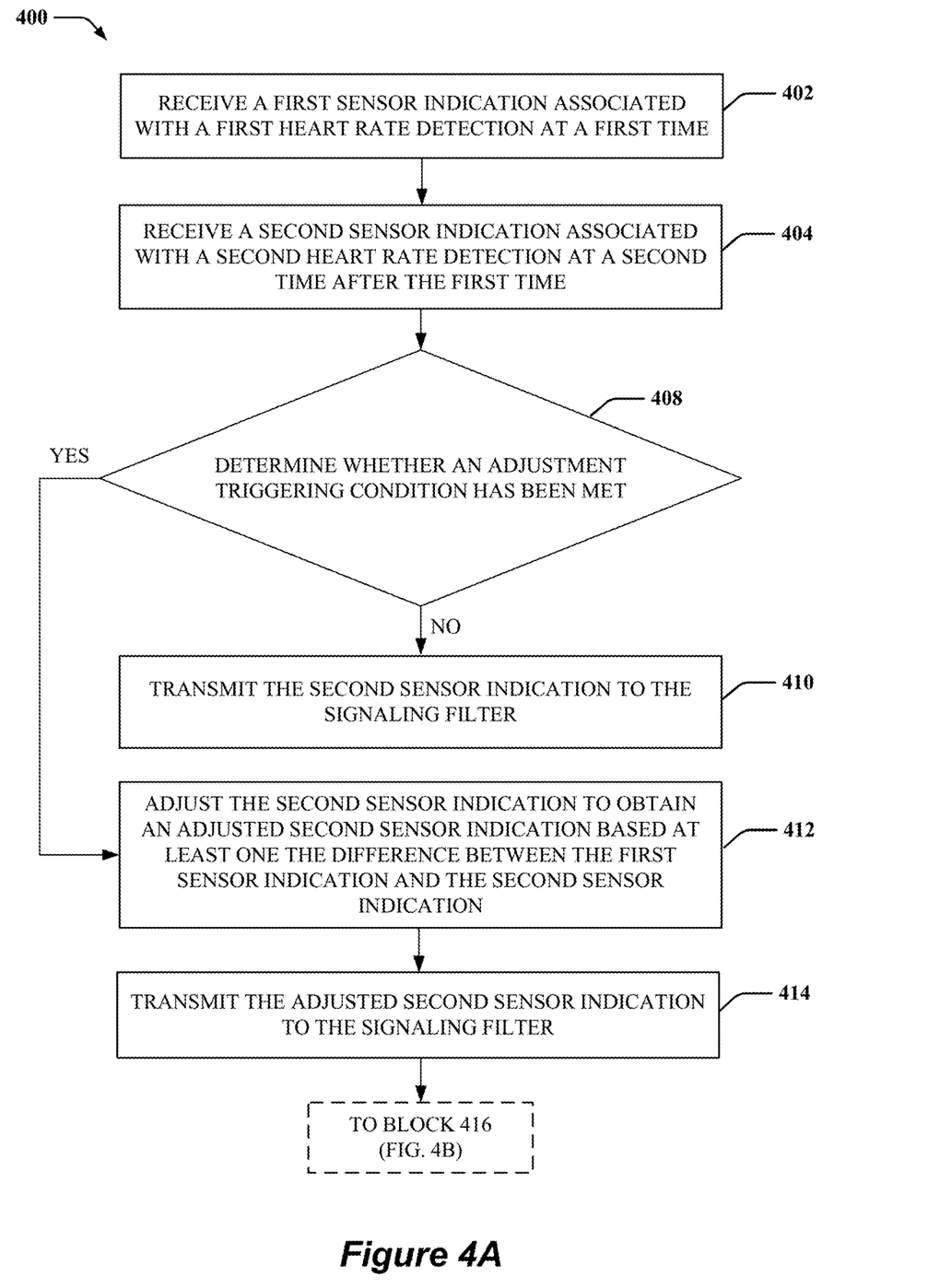
FIGS. 4A and 4B are flow charts of an example of a method of heart rate monitoring and PPG indication discontinuity correction in accordance with some implementations.
Figure 4B:
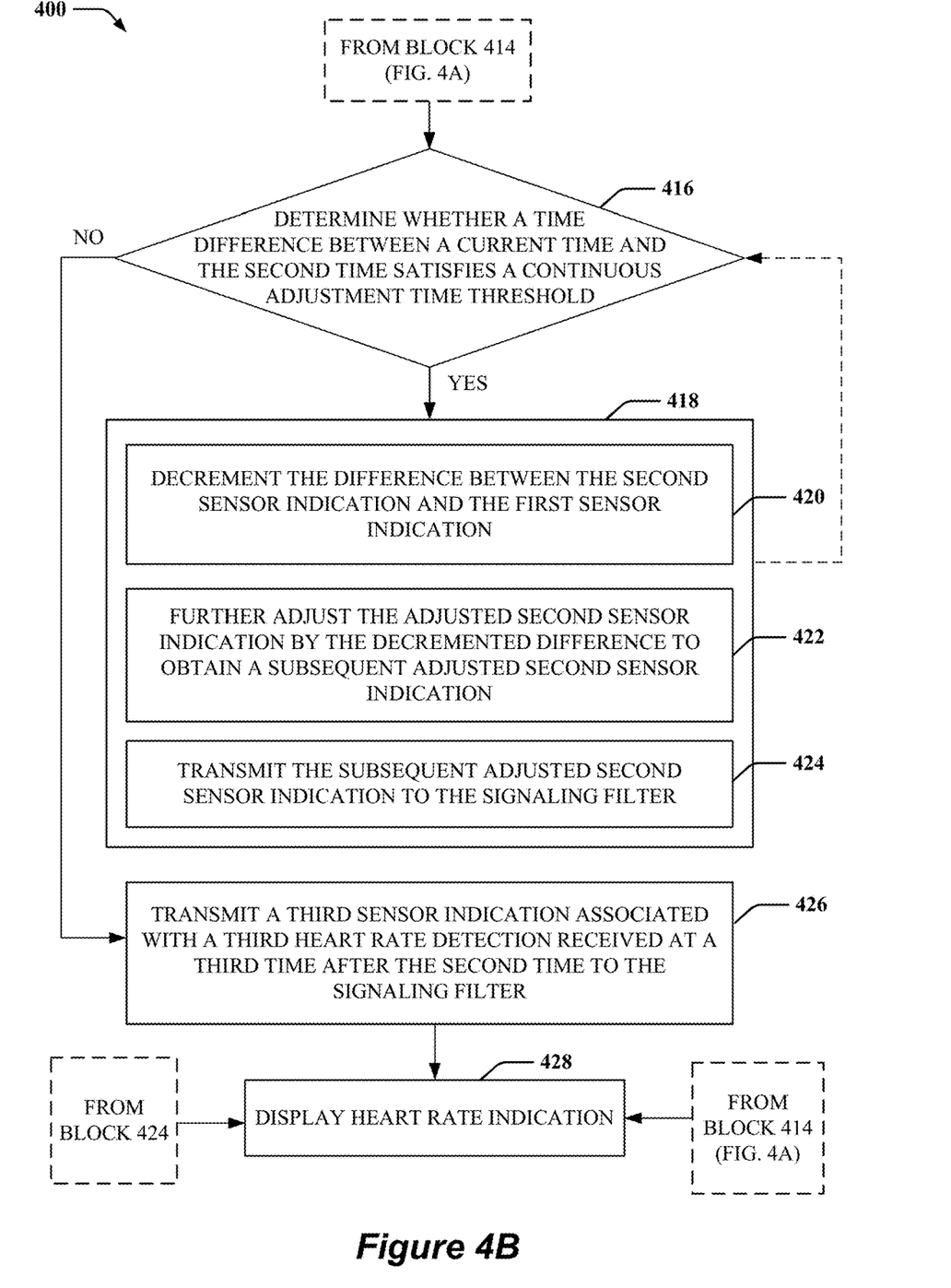

FIGS. 4A and 4B are flow diagrams of an example of a method 400 related to PPG indication discontinuity correction in accordance with various implementations of the present disclosure. Although the operations described below are presented in a particular order and/or as being performed by an example component, it should be understood that the ordering of the actions and the components performing the actions may be varied, depending on the implementation.

Initially, one or more blocks of method 400 may be performed while continuing operation of a signaling filter (e.g., the signaling filter 170, FIG. 1B). At block 402, the method 400 may receive a first sensor indication associated with a first heart rate detection at a first time. For instance, the electronic device 100 (FIG. 1A) may execute the optical emitter and sensor 134 (FIGS. 1A and 1B) to receive a first sensor indication (e.g., the first PPG indication 152, FIG. 1B) associated with a first heart rate detection at a first time.

At block 404, the method 400 may receive a second sensor indication associated with a second heart rate detection at a second time after the first time. For example, the electronic device 100 (FIG. 1A) may execute the optical emitter and sensor 134 (FIGS. 1A and 1B) to receive a second sensor indication (e.g., the second PPG indication 154, FIG. 1B) associated with a second heart rate detection at a second time after the first time. In some implementations, the first sensor indication (e.g., the first PPG indication 152, FIG. 1B) and/or the second sensor indication (e.g., the second PPG indication 154, FIG. 1B) may include an AC component and a DC component.

Further, the first heart rate detection and the second heart rate detection may be part of the same heart rate detection or part of distinct heart rate detections. In some implementations, a heart rate detection may correspond to a pulse detection. The first sensor indication (e.g., the first PPG indication 152, FIG. 1B) and the second sensor indication (e.g., the second PPG indication 154, FIG. 1B) may be adjacent samples that are part of the same pulse or distinct pulses. The second time may be adjacent to the first time or may follow the first time by an amount of time.

At block 408, the method 400 may determine whether an adjustment triggering condition has been met. For instance, the electronic device 100 (FIG. 1A) and/or the PPG indication correction component 110 (FIGS. 1A and 1B) may execute the discontinuity determination component 156 (FIG. 1B) to determine whether the adjustment triggering condition 158 (FIG. 1B) has been met. In some implementations, determining whether the adjustment triggering condition 158 (FIG. 1B) has been met may include determining whether the second sensor indication (e.g., the second PPG indication 154, FIG. 1B) is associated with a discontinuity flag.

The method 400 may proceed to block 410 based on determining that the adjustment triggering condition has not been met. Specifically, at block 410, the method 400 may transmit the second sensor indication to the signaling filter. For example, the electronic device 100 (FIG. 1A) may execute the PPG indication correction component 110 (FIGS. 1A and 1B) to transmit the second sensor indication (e.g., second PPG indication 154, FIG. 1B) not exhibiting distortions to the signaling filter 170 (FIG. 1B).

Otherwise, the method 400 may proceed to block 412 based on determining that the adjustment triggering condition has been met. In particular, at block 412, the method 400 may adjust the second sensor indication to obtain an adjusted second sensor indication based at least on the difference between the first sensor indication and the second sensor indication. For instance, the electronic device 100 (FIG. 1A) may execute the PPG indication correction component 110 (FIGS. 1A and 1B) to adjust the (distorted) second sensor indication (e.g., the second PPG indication 154, FIG. 1B) to obtain an adjusted second sensor indication based at least on a difference value between the first sensor indication (e.g., the first PPG indication 152, FIG. 1B) and the second sensor indication (e.g., the second PPG indication 154, FIG. 1B).

In some implementations, adjusting the second sensor indication (e.g., the second PPG indication 154, FIG. 1B) may include adjusting the DC component of the second sensor indication (e.g., the second PPG indication 154, FIG. 1B) based at least on a difference value between the first sensor indication (e.g., the first PPG indication 152, FIG. 1B) and the second sensor indication (e.g., the second PPG indication 154, FIG. 1B). Further, in some implementations, adjusting the second sensor indication (e.g., the second PPG indication 154, FIG. 1B) may include shifting the DC component of the second sensor indication (e.g., the second PPG indication 154, FIG. 1B) up or down by at least a value less than or equal to the difference value between the second sensor indication (e.g., the second PPG indication 154, FIG. 1B) and the first sensor indication (e.g., the first PPG indication 152, FIG. 1B). Further, the second sensor indication (e.g., the second PPG indication 154, FIG. 1B) may be adjusted without resetting the signaling filter 170 (FIG. 1B).

At block 414, the method 400 may transmit the adjusted second sensor indication to the signaling filter. For example, the electronic device 100 (FIG. 1A) may execute the PPG indication correction component 110 (FIGS. 1A and 1B) to transmit the adjusted second sensor indication to the signaling filter 170 (FIG. 1B).

At block 416, the method 400 may determine whether a time difference between a current time and the second time satisfies a continuous adjustment time threshold. For instance, the electronic device 100 (FIG. 1A) may execute the PPG indication correction component 110 (FIGS. 1A and 1B) to determine whether the time difference value 162 (FIG. 1B) between a current time and the second time satisfies a continuous adjustment time threshold 164 (FIG. 1B).

The method 400 may proceed to block 418 based on a determination that the time difference satisfies the continuous adjustment time threshold. Specifically, at block 418, method 400 may perform one or more of blocks 420, 422, and/or 424. At block 420, method 400 may decrement the difference between the second sensor indication and the first sensor indication. For example, the electronic device 100 (FIG. 1A) may execute the PPG indication correction component 110 (FIGS. 1A and 1B) to decrement the difference value (e.g., time difference value 162, FIG. 1B) between the second sensor indication (e.g., the second PPG indication 154, FIG. 1B) and the first sensor indication (e.g., the first PPG indication 152, FIG. 1B).

Further, at block 422, the method 400 may further adjust the adjusted second sensor indication by the decremented difference to obtain a subsequent adjusted second sensor indication. For instance, the electronic device 100 (FIG. 1A) may execute the PPG indication correction component 110 (FIGS. 1A and 1B) to further adjust the adjusted second sensor indication by the decremented difference value to obtain a subsequent adjusted second sensor indication. In some implementations, the subsequent adjusted second sensor indication may be continuously shifted up or down until the time difference value 162 (FIG. 1B) does not satisfy the continuous adjustment time threshold 164 (FIG. 1B).

Additionally, at block 424, the method 400 may transmit the subsequent adjusted second sensor indication to the signaling filter. For example, the electronic device 100 (FIG. 1A) may execute the PPG indication correction component 110 (FIGS. 1A and 1B) to transmit the subsequent adjusted second sensor indication to the signaling filter 170 (FIG. 1B)

Otherwise, the method 400 may proceed to block 426 based on a determination that the time difference does not satisfy the continuous adjustment time threshold. In particular, at block 426, the method 400 may transmit, to the signaling filter, a third sensor indication associated with a third heart rate detection received at a third time after the second time. For instance, the electronic device 100 (FIG. 1A) may execute the PPG indication correction component 110 (FIGS. 1A and 1B) to transmit, to the signaling filter 170 (FIG. 1B), a third sensor indication (e.g., part of the PPG indications 150) associated with a third heart rate detection received at a third time after the second time. In some implementations, the third sensor indication, which may be a third PPG indication received at a time after block 404, does not exhibit any distortions resulting in PPG signal discontinuity.

Additionally, at block 428, the method 400 may display a heart rate indication associated with at least one of the second sensor indication, the adjusted sensor indication, and/or a third sensor indication on a display of the electronic device. For example, the electronic device 100 (FIG. 1A) may execute the heart rate determination component 108 (FIG. 1A) and the display 112 (FIGS. 1A and 1B) to determine a heart rate indication 160 (FIG. 1B) from the filtered PPG/sensor indication provided by the signaling filter 170 (FIG. 1B), and to subsequently display the heart rate indication 160 (FIG. 1B) associated with at least one of the second sensor indication transmitted in block 410, the adjusted sensor indication transmitted in block 424. Also, for example, the electronic device 100 (FIG. 1A) may execute display 112 (FIGS. 1A and 1B) to display the heart rate indication 160 (FIG. 1B) associated with the third sensor indication transmitted in block 426.

Figure 5:
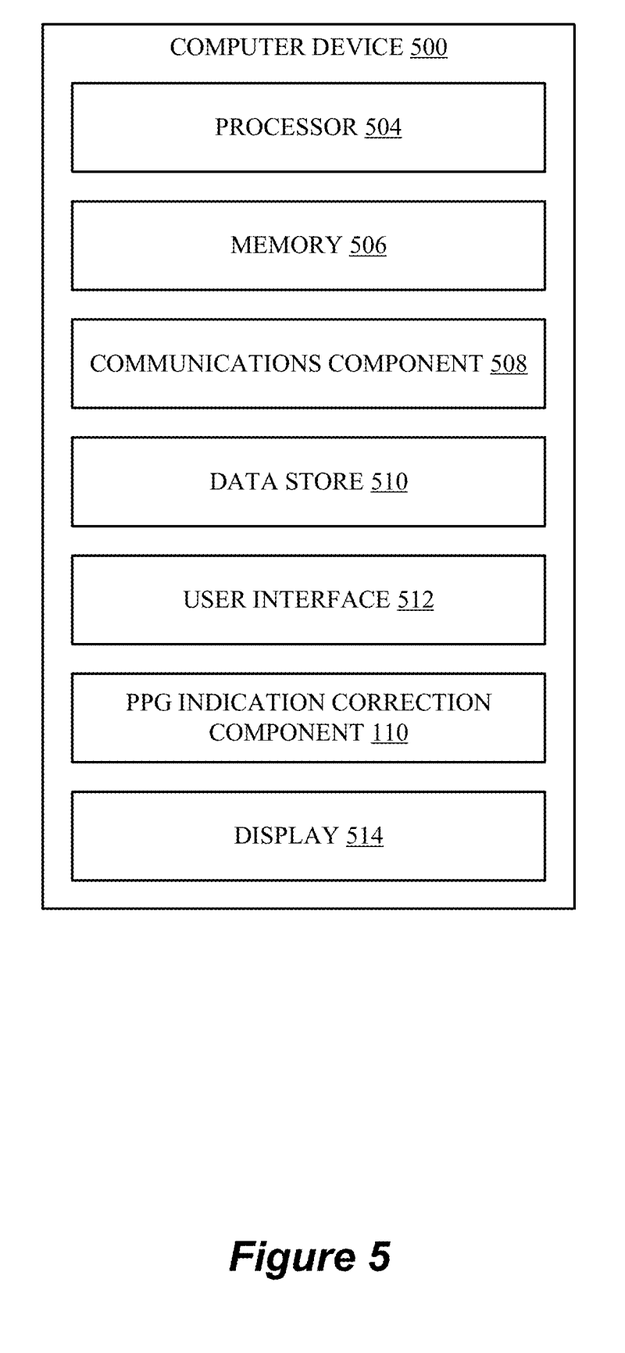
FIG. 5 is a schematic block diagram of an example computer device in accordance with some implementations.

Referring now to FIG. 5, an example computer device 500 includes additional component details as compared to FIGS. 1A and 1B. Computer device 500 may be the same as or similar to or another version of electronic device 100 (FIG. 1A). In one implementation, computer device 500 may include processor 504 for carrying out processing functions associated with one or more of components and functions described herein. Processor 504 can include a single or multiple set of processors or multi-core processors. Moreover, processor 504 can be implemented as an integrated processing system and/or a distributed processing system.

Computer device 500 may further include memory 506, such as for storing local versions of applications being executed by processor 504. Memory 506 can include a type of memory usable by a computer, such as random access memory (RAM), read only memory (ROM), tapes, magnetic discs, optical discs, volatile memory, non-volatile memory, and any combination thereof. Additionally, processor 504 and memory 506 may include and execute PPG indication correction component 110 (FIGS. 1A and 1B).

Further, computer device 502 may include a communications component 508 that provides for establishing and maintaining communications with one or more parties utilizing hardware, software, and services as described herein. Communications component 508 may carry communications between components on computer device 500, as well as between computer device 500 and external devices, such as devices located across a communications network and/or devices serially or locally connected to computer device 500. For example, communications component 508 may include one or more buses, and may further include transmit chain components and receive chain components associated with a transmitter and receiver, respectively, operable for interfacing with external devices.

Additionally, computer device 500 may include a data store 510, which can be any suitable combination of hardware and/or software, that provides for mass storage of information, databases, and programs employed in connection with implementations described herein. For example, data store 510 may be a data repository for adjustment triggering condition 158 (FIGS. 1A and 1B) and continuous adjustment time threshold (FIGS. 1A and 1B). In some implementations, computer device 500 may also include display 514 for displaying content.

Computer device 500 may also include a user interface component 512 operable to receive inputs from a user of computer device 500 and further operable to generate outputs for presentation to the user. User interface component 512 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, user interface component 512 may include one or more output devices, including but not limited to a display, a speaker, a haptic feedback mechanism, a printer, any other mechanism capable of presenting an output to a user, or any combination thereof.

As used in this application, the terms "component," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computer device and the computer device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Furthermore, various implementations are described herein in connection with a device (e.g., electronic device 100 and/or computer device 500), which can be a wired device or a wireless device. A wireless device may be a wearable electronic device, a cellular telephone, a satellite phone, a cordless telephone, a Session Initiation Protocol (SIP) phone, a wireless local loop (WLL) station, a personal digital assistant (PDA), a handheld device having wireless connection capability, a computer device, or other processing devices connected to a wireless modem.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Various implementations or features will be presented in terms of systems that may include a number of devices, components, modules, and the like. It is to be understood and appreciated that the various systems may include additional devices, components, modules, etc., and/or may not include all of the devices, components, modules, etc., discussed in connection with the figures. A combination of these approaches may also be used.

The various illustrative logics, logical blocks, and actions of methods described in connection with the embodiments disclosed herein may be implemented or performed with a specially-programmed one of a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computer devices, e.g., a combination of a DSP and a microprocessor, a plurality of microprocessors, one or more microprocessors in conjunction with a DSP core, or any other such configuration. Additionally, at least one processor may comprise one or more components operable to perform one or more of the steps and/or actions described above.

Further, the steps and/or actions of a method or algorithm described in connection with the implementations disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some implementations, the processor and the storage medium may reside in an ASIC. Additionally, the ASIC may reside in a user terminal. In the alternative, the processor and the storage medium may reside as discrete components in a user terminal. Additionally, in some implementations, the steps and/or actions of a method or algorithm may reside as one or any combination or set of codes and/or instructions on a machine readable medium and/or computer readable medium, which may be incorporated into a computer program product.

In one or more implementations, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

While implementations of the present disclosure have been described in connection with examples thereof, it will be understood by those skilled in the art that variations and modifications of the implementations described above may be made without departing from the scope hereof. Other implementations will be apparent to those skilled in the art from a consideration of the specification or from a practice in accordance with implementations disclosed herein.

What is claimed is:

1. A method of heart rate monitoring at an electronic device, comprising:
    receiving a first sensor indication associated with a first heart rate detection at a first time and a second sensor indication associated with a second heart rate detection at a second time after the first time;
    determining whether a discontinuity exists between the first sensor indication and the second sensor indication;
    in response to the discontinuity not existing, transmitting the second sensor indication to a signaling filter;
    in response to the discontinuity existing, determining whether a time difference between a current time and the second time satisfies a continuous adjustment time threshold;
    in response to the time difference satisfying the continuous adjustment time threshold, adjusting the second sensor indication by a decremented difference between the second sensor indication and the first sensor indication to obtain an adjusted second sensor indication and sending the adjusted second sensor indication to the signaling filter; and
    in response to the time difference not satisfying the continuous adjustment time threshold, sending, to the signaling filter, a third sensor indication associated with a third heart rate detection received at a third time after the second time.

2. The method of claim 1, wherein the second sensor indication includes an alternating current (AC) component and a direct current (DC) component, wherein the adjusting comprises shifting the DC component up or down.

3. The method of claim 1, wherein determining whether the discontinuity exists includes determining whether the second sensor indication is associated with a discontinuity flag.

4. The method of claim 1, wherein the method is performed while continuing operation of the signaling filter in communication with a processor, wherein the adjusting further comprises adjusting without resetting the signaling filter.

5. The method of claim 1, further comprising displaying a heart rate indication associated with one or more sensor indications or one or more adjusted sensor indications on a display of the electronic device.

6. The method of claim 1, wherein the method is performed while continuing operation of the signaling filter in communication with a processor, wherein the signaling filter corresponds to a finite impulse response (FIR) filter that samples and noise filters a sensor indication.

7. The method of claim 1, wherein the electronic device comprises a wearable electronic device having at least one sensor including an optical sensor that generates the first sensor indication, the second sensor indication, and the third sensor indication.

8. The method of claim 1, wherein the first sensor indication, the second sensor indication, and the third sensor indication each correspond to a respective photoplethysmographic (PPG) indication.

9. An electronic device for heart rate monitoring, comprising:
    a memory configured to store data and instructions;
    at least one sensor configured to obtain one or more sensor indications; and
    a processor configured to communicate with the memory and the at least one sensor, wherein the processor is configured to:
        receive, from the at least one sensor, a first sensor indication associated with a first heart rate detection at a first time and a second sensor indication associated with a second heart rate detection at a second time;
        determine whether a discontinuity exists between the first sensor indication and the second sensor indication;
        in response to the discontinuity not existing, transmit the second sensor indication to a signaling filter;
        in response to the discontinuity existing, determine whether a time difference between a current time and the second time satisfies a continuous adjustment time threshold;
        in response to the time difference satisfying the continuous adjustment time threshold, adjust the second sensor indication by a decremented difference between the second sensor indication and the first sensor indication to obtain an adjusted second sensor indication and send the adjusted second sensor indication to the signaling filter; and
        in response to the time difference not satisfying the continuous adjustment time threshold, send, to the signaling filter, a third sensor indication associated with a third heart rate detection received at a third time after the second time.

10. The electronic device of claim 9, wherein the second sensor indication includes an alternating current (AC) component and a direct current (DC) component, wherein to adjust the second sensor indication, the processor is further configured to shift the DC component up or down.

11. The electronic device of claim 9, wherein to determine whether the discontinuity exists, the processor is further configured to determine whether the second sensor indication is associated with a discontinuity flag.

12. The electronic device of claim 9, wherein the signaling filter is configured to filter the one or more sensor indications, wherein the second sensor indication includes an alternating current (AC) component and a direct current (DC) component, wherein the processor is configured to adjust the DC component without resetting the signaling filter.

13. A non-transitory computer-readable medium storing instructions executable by a processor of an electronic device for heart rate monitoring, comprising at least one instruction for causing the electronic device to:

receive a first sensor indication associated with a first heart rate detection at a first time and a second sensor indication associated with a second heart rate detection at a second time;

determine whether a discontinuity exists between the first sensor indication and the second sensor indication;

in response to the discontinuity not existing, transmit the second sensor indication to a signaling filter;

in response to the discontinuity existing, determine whether a time difference between a current time and the second time satisfies a continuous adjustment time threshold;

in response to the time difference satisfying the continuous adjustment time threshold, adjust the second sensor indication by a decremented difference between the second sensor indication and the first sensor indication to obtain an adjusted second sensor indication and send the adjusted second sensor indication to the signaling filter; and in response to the time difference not satisfying the continuous adjustment time threshold, send, to the signaling filter, a third sensor indication associated with a third heart rate detection received at a third time after the second time.

14. The non-transitory computer-readable medium of claim 13, wherein the second sensor indication includes an alternating current (AC) component and a direct current (DC) component, wherein to adjust the second sensor indication, the at least one instruction further causes the electronic device to shift the DC component up or down.

15. The non-transitory computer-readable medium of claim 13, wherein to determine whether the discontinuity exists, the at least one instruction further causes the electronic device to determine whether the second sensor indication is associated with a discontinuity flag.

16. The non-transitory computer-readable medium of claim 13, wherein to adjust the second sensor indication, the at least one instruction further causes the electronic device to adjust without resetting the signaling filter in communication with the processor.

17. The electronic device of claim 9, further comprising a display, wherein the processor is configured to cause presentation of a heart rate indication associated with one or more sensor indications or one or more adjusted sensor indications on the display.

18. The electronic device of claim 9, wherein the signaling filter is configured to filter the one or more sensor indications, wherein the signaling filter corresponds to a finite impulse response (FIR) filter that samples and noise filters a sensor indication.

19. The electronic device of claim 9, further comprising a wearable electronic device having an optical sensor that generates the first sensor indication, the second sensor indication, and the third sensor indication.

20. The electronic device of claim 9, wherein the first sensor indication, the second sensor indication, and the third sensor indication each correspond to a respective photoplethysmographic (PPG) indication.

* * * * *